(12) United States Patent
Jarron et al.

(10) Patent No.: US 8,598,536 B2
(45) Date of Patent: Dec. 3, 2013

(54) APPARATUS AND METHOD FOR MEDICAL IMAGING

(75) Inventors: Pierre Jarron, Saint Julien en Genevois (FR); Francis Anghinolfi, Thoiry (FR); Jorgen Christiansen, Segny (FR)

(73) Assignee: CERN—European Organization For Nuclear Research, Geneva (CH)

( * ) Notice: Subject to any disclaimer, the term of this patent is extended or adjusted under 35 U.S.C. 154(b) by 1048 days.

(21) Appl. No.: 12/444,295

(22) PCT Filed: Nov. 2, 2006

(86) PCT No.: PCT/EP2006/010524
§ 371 (c)(1),
(2), (4) Date: Nov. 20, 2009

(87) PCT Pub. No.: WO2008/040384
PCT Pub. Date: Apr. 10, 2008

(65) Prior Publication Data
US 2010/0078569 A1    Apr. 1, 2010

(30) Foreign Application Priority Data
Oct. 4, 2006 (DE) .......................... 10 2006 046 973

(51) Int. Cl.
*G01J 1/42* (2006.01)
*G01T 1/166* (2006.01)

(52) U.S. Cl.
USPC ...................... 250/395; 250/363.04

(58) Field of Classification Search
USPC ............................ 250/395, 363.04
See application file for complete search history.

(56) References Cited

U.S. PATENT DOCUMENTS

| | | | | |
|---|---|---|---|---|
| 4,077,030 A | * | 2/1978 | Helava | ................... 340/870.13 |
| 5,672,877 A | | 9/1997 | Liebig et al. | |
| 6,448,559 B1 | | 9/2002 | Saoudi et al. | |
| 2003/0146388 A1 | | 8/2003 | Wainer | |
| 2004/0114469 A1 | * | 6/2004 | Duffner et al. | ................. 368/113 |
| 2006/0131508 A1 | * | 6/2006 | Burr et al. | ................. 250/370.11 |

OTHER PUBLICATIONS

International Search Report dated Jun. 19, 2007, 3 pgs.

* cited by examiner

*Primary Examiner* — David Porta
*Assistant Examiner* — Mindy Vu
(74) *Attorney, Agent, or Firm* — RatnerPrestia

(57) ABSTRACT

The present invention discloses an apparatus for use in medical imaging including a readout circuit having an input for receiving a detection signal corresponding to a photon hitting a radiation detector, wherein the readout circuit is adapted to output, in response to receiving said detection signal, a pulse signal having a leading edge encoding a time-stamp of said photon and a width encoding the energy of said photon. A method of reading out detection signals from a radiation detector of a medical imaging apparatus is also provided.

39 Claims, 12 Drawing Sheets

APPARATUS AND METHOD FOR MEDICAL IMAGING

BACKGROUND OF THE INVENTION

The present invention relates to an apparatus for use in medical imaging comprising a readout circuit having an input for receiving a signal corresponding to a photon hitting a radiation detector. The application further relates to a detector assembly and to a combined PET-CT apparatus as well as to a method according to the preamble of claim 27.

Medical imaging techniques employing radiation detectors for detecting photons for example comprise Positron Emission Tomography (PET), X-ray computed tomography (CT), Single Photon Emission Computed Tomography (SPECT) and γ cameras. While the invention is not limited to any specific type of medical imaging, for illustrative purposes we shall explain the invention with specific reference to PET.

PET is a nuclear medicine tomographic imaging technique using γ rays. To conduct a scan, a short-lived radioactive tracer isotope which decays by emitting a positron and which has been chemically incorporated into a metabolically active molecule is injected into the patient, typically into the blood circulation. There is a waiting period while the metabolically active molecule becomes concentrated in the tissues of interest. Thereafter, the patient is placed in an imaging scanner.

As the radioisotope undergoes positive beta decay, it emits a positron which after a short travel encounters and annihilates with an electron, thereby producing a pair of γ-photons having an energy of 511 keV and usually traveling in opposite directions. The γ-photons are detected by a radiation detector typically comprised of a scintillator and an associated photodetector. The signal from the photodetector must then be readout by a suitable readout circuit. PET depends on simultaneous or coincident detection of the pair of γ-photons. Photons which do not arrive in pairs (i.e. within a few nanoseconds) are ignored.

Since most of the γ-photons are emitted at 180 degrees from one another during electron-positron annihilation, the source of radiation can be located along a straight line connecting the two radiation detector sites at which coinciding hits are detected. If the response of the radiation detector and the corresponding reader circuit is fast enough, it is moreover possible to calculate the location of the radiation source on said line from a difference in the arrival times. This method is called "time-of-flight" (TOF) measurement. However, this would require a time resolution of the measurement in the picosecond range which is currently difficult to achieve. Instead, typically statistics are collected from tens-of-thousands of coincidence events and equations for the total activity of each parcel of the tissue of interest along the above mentioned straight line is solved, such that a map of radioactivities can be constructed and outputted. Clearly, if time-of-flight information is available, the statistics needed for producing a high quality image would be smaller, and accordingly, a smaller dose of radioactive tracer isotope could be used which would be healthier for the patient. A prime goal of the above mentioned apparatus is therefore to provide a very fast readout channel allowing for measurements in the picosecond rather than nanosecond range.

FIG. 1 schematically shows an electronic readout channel according to prior art which is currently used in PET-systems. The readout channel of FIG. 1 comprises and avalanche photo diode (APD) array element 10 receiving light from a scintillator (not shown) upon a photon hitting the scintillator. The APD array element outputs an analog signal which is processed by a preamplifier 12 and a shaper 14 and is then inputted into an analog-to-digital (A/D) converter 16. The A/D converter 16 is clocked at high frequency (typically 40 to 100 MHz) and outputs a digital signal. The digital signal is then transferred to a FIFO buffer 18 and to a coincidence processor 20 for detecting coincidence of two γ-photons which can be assigned to a common electron-positron annihilation. The digital samples are processed by an algorithm implemented in a digital filter that determines the time-stamp and a signal of the amplitude. The architecture of FIG. 1 continuously samples analog signals and produces large data sets that due to their large size are generally processed off-line further down the image processing chain.

The prior art readout architecture of FIG. 1, however, has the following disadvantages.

1. Retrieving time information for sampled data requires additional hardware and algorithms that increase processing time and hardware costs.
2. The precision of the sampling of the signals depends on the signal shape. Shape variations lead to a decrease of precision in the evaluation of the timing of the corresponding event, in particular since PET events are randomly distributed over time and thus uncorrelated with the sampling clock cycle.
3. To obtain a higher timing precision and event counting rate, the clock frequency of the sampling A/D converter must increase which might lead to significant data overflow problems.
4. Modern PET scanners and in particular whole-body-PET scanners with a large field of view use increasingly more detector rings containing highly segmented arrays of scintillating crystals each being as small as 2×2 mm$^2$, such that the number of required front-end electronic readout channels easily increases to more than one hundred thousand. For such a large number of channels the cost, power dissipation and complexity of signal processing using the readout architecture of FIG. 1 becomes extremely demanding.

As mentioned above, the invention is not limited to PET-imaging, and accordingly, in FIG. 2 a prior art readout architecture for X-ray detection is shown. In the shown front-end electronics of an X-ray CT-scanner system an APD-array element 10 collects light from a scintillator (not shown) hit by an X-ray photon and generates an analog current signal. The analog current signal is amplified by a current amplifier 22, and the amplified current is integrated by an integrator 24. The integral of the current received in a given time frame is proportional to the number of X-ray photons hitting the detector in said time frame. The integrated signal is then digitized by an A/D converter 26 and outputted to an image reconstruction processing logic. Note that in the context of this application, the term "logic" refers to any kind of hardware, software or combination thereof providing the respective logic function.

PET-scans and CT-scans are preferably performed simultaneously since they give in combination both anatomic and metabolic information. That is, modern PET-scanners are available with integrated high-end CT-scanners. Since the two types of scans can be performed sequentially without the patient having to move between the scans, the two sets of images are precisely registered such that areas of the PET imaging can be precisely correlated with the anatomy provided by the CT-images. Note however, that the readout technologies of FIGS. 1 and 2 are incompatible with one another such that it is not possible to perform a simultaneous PET-CT co-registration with a common detector head.

In other prior art PET systems the photon arrival time is detected using a constant fraction discriminator (CFD) that extracts the precise time-stamp of photon arrival for coincidence and time-of-flight measurement. CFDs are for example known for the detection of scintillator pulses having identical rise times which are much longer than the desired temporal resolution. Accordingly, it is not sufficient to use a simple threshold triggering which would introduce a dependence of signal peak height and trigger time, an effect which is called "time walk" and is described more in detail below. Instead, according to CFD triggering is not performed on a fixed threshold but on a constant fraction of the total peak height yielding trigger times independent from peak heights.

An example of a CFD circuit is shown in FIG. 3. A CFD circuit used for PET-applications is for example described in detail in "An Analog Signal Processing ASIC for a Small Animal LSO-APD PET Tomograph", V. Ch. Spanoudaki, D. P. McElroy and S. I. Ziegler, Nuclear Instruments and Method in Physics Research, Section A, in press, such that a detailed explanation is omitted.

However, a readout circuit based on a CFD has two main disadvantages. Firstly, the integration of a fast CFD circuit in a monolithic CMOS that is now currently done for electronics system turns out to be difficult for timing precision of better than 100 ps. Also, the CFD circuits are quite expensive if produced in the necessary amount. Secondly, a CFD-based readout architecture only provides a time-stamp but not the signal amplitude, such that PET events cannot be reliably distinguished from background events and Compton events cannot be reconstructed.

Accordingly, it is an object of the current invention to provide a method and an apparatus for use in medical imaging that overcome the above mentioned drawbacks.

SUMMARY OF THE INVENTION

This object is achieved by an apparatus according to claim 1 and a method according to claim 27. Preferable embodiments are defined in the dependent claims.

According to the invention, the readout circuit of the apparatus is adapted to output in response to receiving the detection signal a pulse signal having a leading edge encoding a time-stamp of the photon and a width encoding the energy of the photon. That is, the information of interest, namely the time-stamp and the energy is encoded in a simple digital pulse signal. Accordingly, the invention compares favorably with an apparatus based on digitizing detection signals where large amounts of data are produced, and it is at the same time is superior to CFD techniques in providing both time-stamp and energy information. Moreover, such a pulse signal can be easily and rapidly processed by a time-to-digital converter (TDC), as will be explained below, such that images can be generated in real time and that events can be recorded at extremely high rates.

In a preferred embodiment, the apparatus further comprises means for correcting the time-stamp of the pulse signal based on the width of the pulse signal. Said means may be configured to estimate a time-walk of the pulse signal from the width of the pulse signal and to subtract the time-walk from the time-stamp, as will be explained in greater detail below.

In a preferred embodiment, the readout circuit is adapted for encoding the time-stamp and energy of one or more types of photons selected among a group consisting of: γ-photons as generated during electron-positron annihilation, X-ray photons of a wavelength suitable for X-ray CT, photons in the visible range, and γ-photons as emitted by radio pharmaceuticals suitable for γ camera imaging or SPECT. That is, the apparatus cannot only be adapted for a particular type of photon suitable for medical imaging, but it can moreover be simultaneously adapted for two different types of photons. For example, the apparatus may be suitable for reading out both detection signals corresponding to CT X-ray photons and detection signals corresponding to PET photons. Accordingly, in such a configuration the apparatus allows for a single detection head or front-end which is capable of detecting both, CT and PET signals.

In a preferred embodiment, the readout circuit is a discriminator circuit configured to compare the detection signal to a threshold value, where the leading edge of the pulse signal corresponds to the time the detection signal first exceeds said threshold value and the trailing edge of the pulse-signal corresponds to the time the detection signal drops below said threshold value. As will be described in more detail below, such a discriminator circuit can be manufactured at low cost and is capable of operating at very high speed sufficient for time recording well in the picosecond range.

In a preferred embodiment, the apparatus comprises a filter circuit for filtering the pulse signals according to their width. In particular, the filter may comprise at least one gate-delay circuit comprising an AND-gate to which a fraction of the pulse signal and a delayed fraction of said pulse signal is fed, which is delayed by a predetermined time-delay. Such a filter is simple to implement and at the same time effective in discriminating between signals corresponding to different types of events or different types of photons.

In a preferred embodiment the filter circuit comprises a PET-filter configured to pass pulse signals having a width corresponding to the energy of γ-photons emitted during electron-positron annihilation. In one embodiment, the PET-filter blocks pulse signals having a width corresponding to an energy of less than 350 keV, and preferably, less than 400 keV.

Alternatively or additionally, the filter circuit may comprise a CT-filter, configured to allow pulse signals having a width corresponding to the energy of X-ray photons suitable for CT to be countered by a counter. With these types of filters, it is possible to use the same readout circuit for both CT and PET events and to distinguish between the signals downstream. In particular, this allows for a combined PET-CT apparatus with a common detector head for both, CT and PET signals.

In a preferred embodiment, the apparatus comprises a filter for distinguishing pulse signals corresponding to two or more detection signals corresponding to individual X-ray photons that are overlapping in time. In particular, the filter may comprise a number of n gate-delay circuits as defined above connected in parallel, where n is an integer greater or equal than 2, wherein the predetermined time-delays of the gate-delay circuits respectively correspond to an expected width of the pulse signal for one, two, . . . , n overlapping X-ray detection signals. This filter will allow for a so-called pile-up correction occurring when CT photons at a given detector segment overlap in time. Such pile-up will be likely to occur with an increasing X-ray intensity. This filter allows to avoid the corruption of the X-ray image due to significant overlapping of X-ray photons at higher X-ray intensities.

Preferably, the apparatus further comprises a time-to-digital (TDC) converter connected to receive the pulse signal and configured to measure the arrival time of both, the leading and trailing edge of the pulse signal. The TDC may further be configured to store the leading edge time measurement and the pulse width in a local channel FIFO register.

The invention further relates to a detection assembly for a medical imaging apparatus, and in particular, a PET-apparatus or a combined PET-CT-apparatus comprising a multitude of apparatuses according to one of the embodiments described above. The detection assembly may comprise a multitude of detector elements, each detector element comprising an array of radiation detectors providing a number of channels for outputting detection signals and a corresponding number of apparatuses as defined above providing electronic channels for reading out the detection signals.

Preferably, the detection assembly comprises a control unit configured or programmed for detecting coincidence of detection signals. Preferably, the control unit is further configured or programmed to calculate the location of an electron-positron annihilation using a difference in time-stamp of the coinciding events.

In a preferred embodiment of the detection assembly, some or all of the multitude of detector elements are connected to a common reference clock.

Finally, one aspect of the invention relates to combined PET-CT apparatus comprising an X-ray generator suitable for CT and a detection assembly according to one of the embodiments described above.

DESCRIPTION OF THE PREFERRED EMBODIMENT

Figure 1:
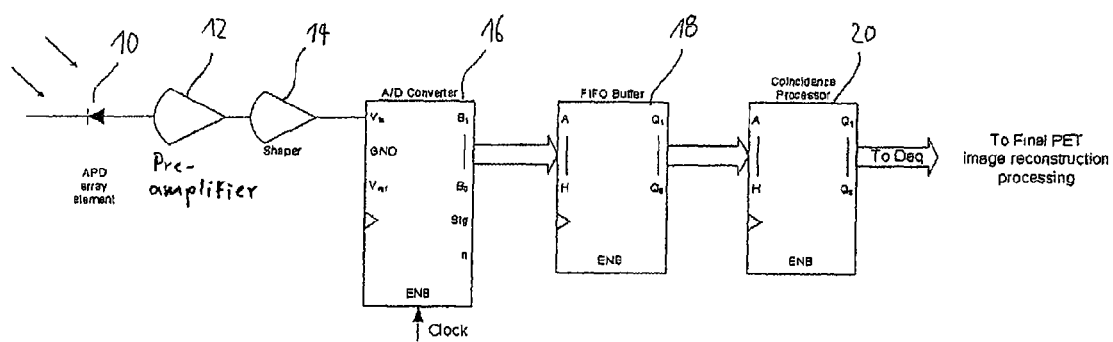
FIG. 1 shows a prior art readout architecture for a PET apparatus based on sampling amplified analog photodetector signals with an A/C converter and processing the sampled signals with a digital processor which extracts time-stamp and energy amplitude.
Figure 2:
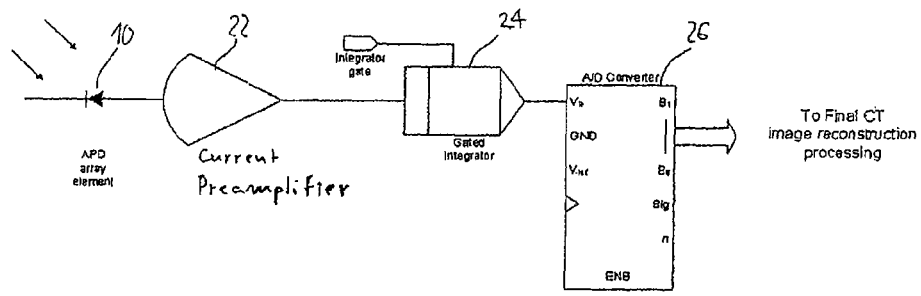
FIG. 2 shows a prior art readout architecture for measuring an X-ray photon intensity based on a current signal integration of the photodetector sensing light produced by a scintillator placed in front of the photodetector during one CT image frame.
Figure 3:
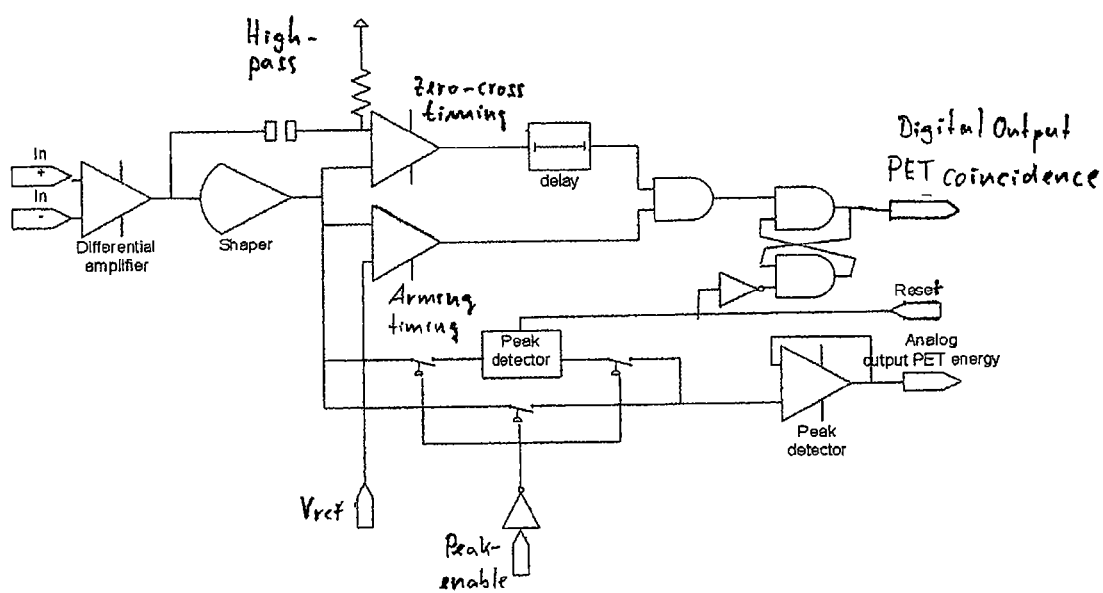
FIG. 3 shows a prior art readout architecture for a PET-apparatus based on a CFD discriminator and a pulse peak detector.

For the purposes of promoting an understanding of the principles of the invention, reference will now be made to the preferred embodiment illustrated in the drawings, and specific language will be used to describe the same. It will nevertheless be understood that no limitation of the scope of the invention is thereby intended, such alterations and further modifications in the illustrated devices and method and such further applications of the principles of the invention as illustrated therein being contemplated as would normally occur now or in the future to one skilled in the art to which the invention relates.

Figure 4:
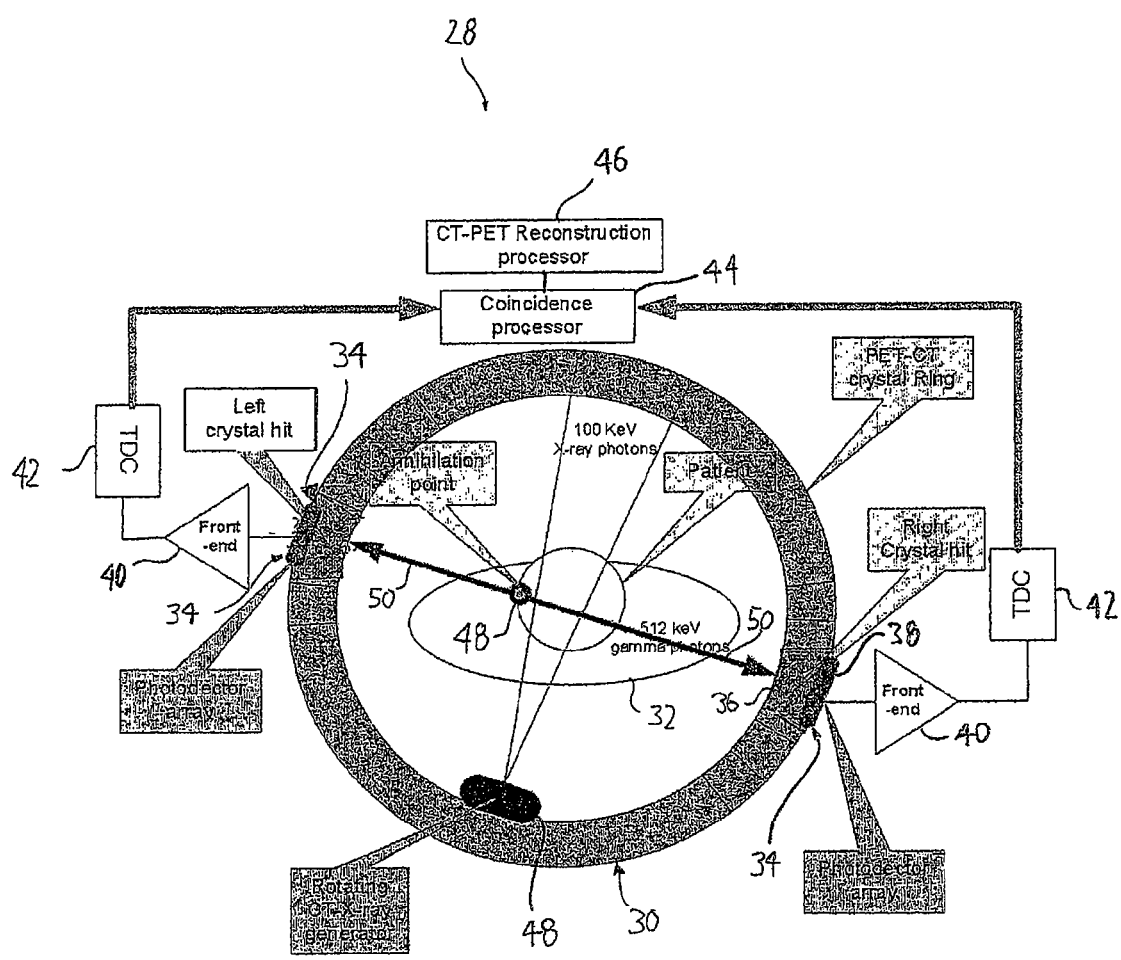
FIG. 4 shows a schematic illustration of a combined PET-CT apparatus according to an embodiment of the invention.

In FIG. 4 a combined PET-CT-apparatus 28 according to an embodiment of the invention is schematically shown. The PET-CT-apparatus 28 comprises a plurality of detector rings 30, one of which is shown in FIG. 4. The detector ring is surrounding a body of a patient 32 which is subject to a combined PET- and CT-examination. The detector ring 30 is comprised of a multitude of detector elements 34, of which only two are shown schematically in FIG. 4.

Each detector element comprises a scintillator array 36 and a photodetector array 38 located adjacent to the scintillator array 36. In the shown embodiment, the photodetector array 38 is comprised of an array of avalanche photodiodes.

Each of the photodetector arrays 38 is connected with a front end or readout circuitry 40 providing a readout architecture to be described in greater detail below. A time-to-digital converter (TDC) 42 is connected to each front-end 40. All of the TDCs are connected to a coincidence processor 44 which in turn is coupled with a PET-CT reconstruction processor 46. The combined PET-CT apparatus 28 of FIG. 4 further comprises a rotating X-ray generator 48 for generating X-rays suitable for CT.

In the following, the general function of the combined PET-CT apparatus 28 of the embodiment of FIG. 4 is described. Before the patient 32 is placed in the detector ring 30, a short-lived radioactive tracer isotope that has been chemically incorporated into a metabolically active molecule is injected to the patient 32. There is a waiting period while the metabolically active molecule, such as fluorodeoxyglucose, becomes concentrated in the tissues of interest. Upon the decay of the radioactive tracer isotope a positron is emitted. The positron will after a travel of at most a few millimeters encounter an electron and annihilate with the same at an annihilation point indicated at 48 in FIG. 4.

Upon the electron-positron annihilation, two 511 keV γ-photons are emitted under an angle of 180° from one another. The γ-photons will be detected at two different detector elements 34. Using the readout circuitry of the front-end 40 and the TDC 42, the arrival time, also called time-stamp, and the energy of the detected photons 50 are determined. The energy of the measured photon can be used to determine whether the photon has the expected energy and is therefore due to the electron-positron annihilation and not for example due to background noise. The time-stamps of the detection events are used by the coincidence processor 44 to determine whether two detected events are coinciding in time such that they can be assigned to a common annihilation process.

Note that the two photons 50 would have exactly the same time-stamp only if the annihilation point was exactly at the center of the detector ring 30. With reference to FIG. 4, the annihilation point 48, however, is closer to the left detector element 34 than to the right detector element 34 such that the time-stamp of the photon detected at the left detector 34 will be slightly earlier than the time-stamp of the photon detected by the right detector element 34. Such events will still be detected as coinciding by the coincidence processor 44. In fact, the difference in time-stamp is used by the PET-CT reconstruction processor 46 to calculate at which location along the line of propagation of the photons 50 the annihilation took place. Such a type of measurement is called "time-of-flight" (TOF) measurement for obvious reasons. From the coincidence information and time-of-flight information the PET-CT reconstruction processor 46 can generate a 3 D image of positron emission events which can for example be used in clinical oncology for the medical imaging of tumors and the search for metastases.

Simultaneously with the PET scan a CT scan is performed using the rotating X-ray generator 48. The X-ray photons will be detected by the same detector elements 34 as the PET-γ-photons, such that the same scintillator 36, photodetector array 38 and most of the front-end 40 can be used for the X-ray imaging simultaneously as well. Since the readout architecture provides the energy of the event in addition to its time-stamp, and since the X-ray photons are on the order of 100 keV and therefore roughly a fifth of the energy of the PET-γ-photons, the readout architecture can discriminate between the two types of events, as will be shown in greater detail below. The PET-CT reconstruction processor can then use the information from the PET and the CT scans of the same patient to thereby generate two sets of images which are precisely registered so that areas of abnormality on PET-imaging can be perfectly correlated with the patient's anatomy imaged by CT.

As is clear from the above discussion, the electronic readout channels used for the PET-CT apparatus 28 must have a number of specific properties. In particular, the readout architecture must be capable of operating fast enough such as to produce data of a precision in the picosecond range to allow for TOF measurements and also fast enough to manage high photon rates. Also, since there are a multitude of detection channels (a number of 100,000 can easily be reached), the readout architecture should be low priced and have limited power dissipation. In addition, the amount of data produced during readout should be kept low such that it is possible to generate the images "on the fly". Due to data processing capacity, if the amount of data produced is too large, the only possibility is to store the data and construct the images offline.

In order to meet the above prerequisites, an aspect of the invention deals with a novel readout architecture which will be described in the following in more detail.

Figure 4A:
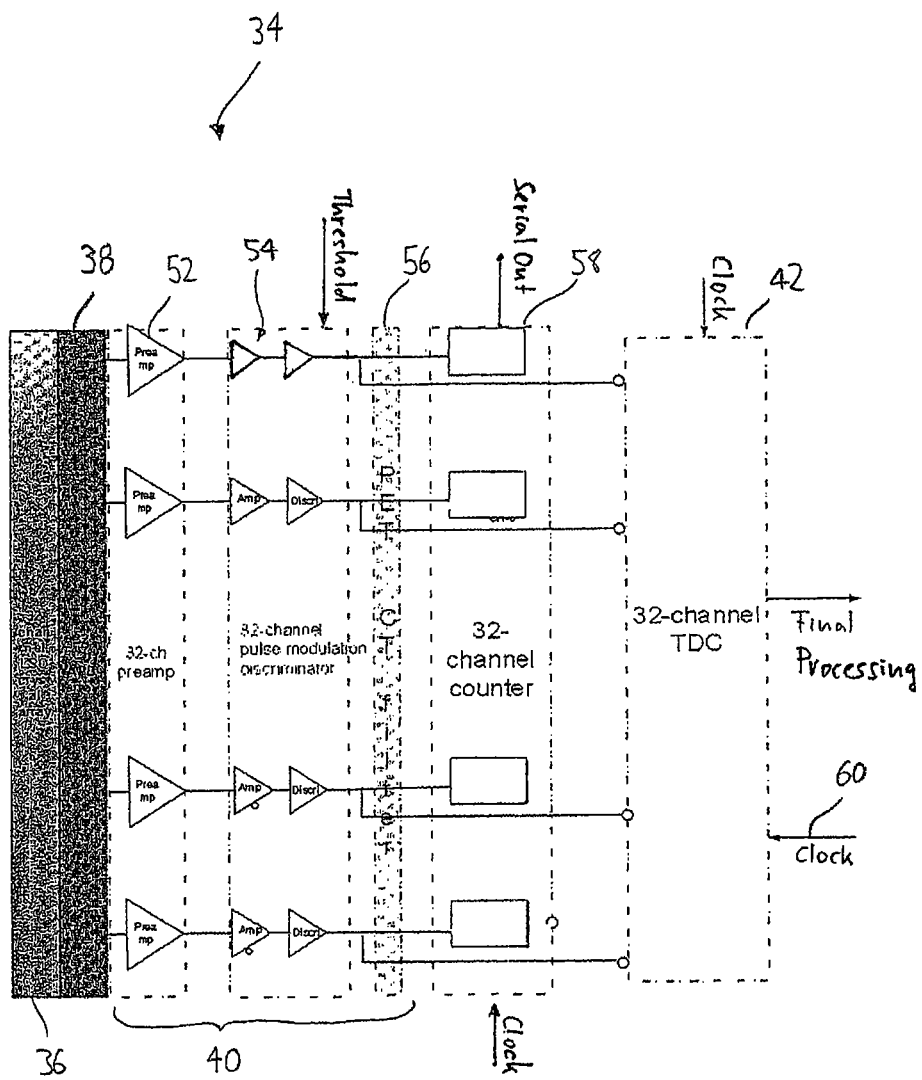
FIG. 4A is a block diagram showing a combined PET-CT readout architecture employing a pulse modulation discriminator and a TDC according to an embodiment of the invention.

In FIG. 4A, a block diagram of a detector element 34 and a corresponding readout architecture is shown. The detector element 34 provides for 32 channels, of which in FIG. 4A only four are shown. The detector element 34 comprises a 32 channel LSO-crystal array attached to a 32 channel APD-array 38. The output of each APD-element of the APD-array 38 is connected to an electronic readout channel. Each electronic readout channel comprises a preamplifier 52, a pulse modulation discriminator circuit 54 and a PET-CT-filter circuit 56 located downstream of the pulse modulation discriminator 54. Each pulse modulation discriminator 54 receives an analog signal corresponding to a preamplified detection signal from a photon hitting the scintillator 36 and generates there from a square pulse signal having a leading edge encoding a time-stamp for that photon and a width encoding the energy of the photon. Since the width of the pulse signal is modulated according to the energy of the detected photon, the pulse signal may be termed a "pulse width modulated" signal.

The filter 56 discriminates the pulse signals outputted from the pulse modulation discriminator 54 by their pulse widths, that is, by the energy of the corresponding photon. In the embodiment shown in FIGS. 4 and 5, the filter 56 discriminates between pulses arising from X-ray photons and pulses arising from PET-γ-photons. Pulses corresponding to X-ray photons are channeled to a counter 58 which is suitable for counting the number of X-ray photons detected in the respective channel within a given time-frame, thus providing one pixel of an X-ray image. The filter further directs pulse signals corresponding to PET-γ-photons to a TDC-circuit 42 in which the arrival time of both, the leading and trailing edge of the pulse signal are measured. In a preferred embodiment, each TDC 42 is receiving a global reference clock signal 60. This global clock reference signal will allow to compare time-stamps from different channels, and in particular, from channels of different regions of the detector ring 30, which is important for coincidence and TOF-measurements.

Figure 5:
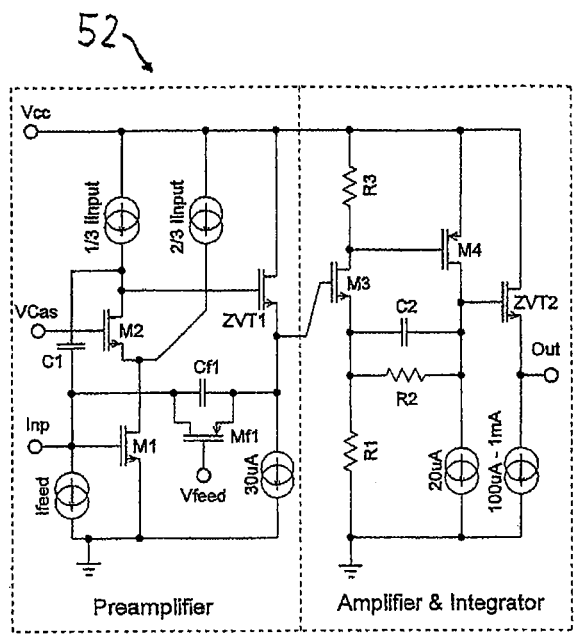
FIG. 5 shows an example of a preamplifier.

In FIG. 5 a circuit diagram of one channel of the 32 channel preamplifier 52 of FIG. 4A is shown in detail. In the shown embodiment, the preamplifier circuit 52 is implemented in a standard 0.25 μm CMOS technology. The circuit is a general purpose test amplifier suitable for the readout of silicon strip detectors and has already been used in LHC experiment. For a detailed discussion, reference is made to J. Kaplan, W. Dabrowski, "Fast CMOS Binary Front-End for Silicon Strip Detectors at LHC Experiments", IEEE Trans. Nucl. Sci., Vol. 52, No. 6, pp. 2713-2720, December 2005. The basic chip consists of 16 channels of charge sensitive amplifiers and analogue output drivers. Each channel comprises a fast transimpedance preamplifier working with an active feedback loop, wherein one stage of the amplifier-integrator circuit provides 22 ns peaking time, and an output buffer capable to drive up to 10 pF output load capacitance.

As can be seen from FIG. 5, the preamplifier is based on a classical cascode configuration with the NMOS input transistor of size 1000 μm/0.5 μm optimized for input capacitances in the range of 10 pF. The active feedback circuit employed in the design offers much lower parasitic capacitance of the feedback loop and consequently a higher bandwidth of that stage, when compared to a resistive feedback loop using low-resistivity poly-silicon resistors. The contribution of the active feedback circuit to ENC noise for a nominal feedback current of 800 nA is about 400 e-, which is still acceptable in view of the expected series noise contribution from the input transistor which is loaded with an external capacitance of 10 pF, which is the typical capacitance of an APD array element. The nominal bias current of the input transistor can be adjusted between 300 μA to 600 μA, which provides a way to optimize noise against the power consumed by this stage, as will be explained below.

The following integrator stage comprises a voltage amplifier consisting of two cascaded common source amplifiers enclosed with resistive feedback. The whole preamplifier-shaper circuit has a gain of about 28 mV/fC and a peaking time of 22 ns. The dynamic range of the whole chain is in the range of 800 mV which is equivalent to 30 fC signal charge. Note that in principle the dynamic range of the amplifier in terms of amplitude response linearity is limited to about 30 fC. However, the pulse width modulation discriminator 54 (described in more detail below) senses input charges that are proportional to a signal pulse shape area. Accordingly, a dynamic range up to 150 fC can be achieved by this charge sensing method.

Figure 5A:
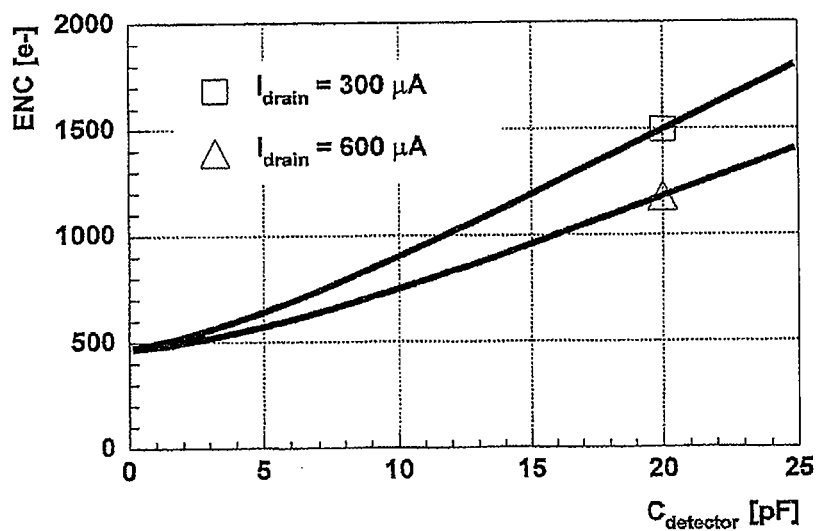
FIG. 5A shows a diagram of ENC as a function of the input capacitance for two different input transistor bias currents calculated for an 800 nA feedback bias current.

FIG. 5A shows calculated ENC noise as a function of the input capacitance for two different values of the input transistor bias and for a nominal value of the feedback bias current of 800 nA. As can be seen from FIG. 5A, for a higher input transistor bias $I_{drain}$, a smaller ENC can be achieved. That is, generally, one may have to find a compromise between ENC noise and power consumption. Since the power consumption is not of primary importance with regard to the medical imaging apparatus 28, a bias current of 600 µA is acceptable, and accordingly, achievable noise levels for typical detector capacitances of about 10 pF are below 800 e-ENC.

Moreover, since a typical value of threshold applied to the pulse width modulation discriminator 54 is in the range of 1 fC, the noise hit rate caused by the electronics is negligible. Note that in the apparatus 28 of the current embodiment, the minimum signal to be detected originates from 100 KeV X-ray photons, which in a typical setup correspond to a charge of about 6 fC, while the PET signal in the same setup corresponds to about 30 fC.

Figure 6:
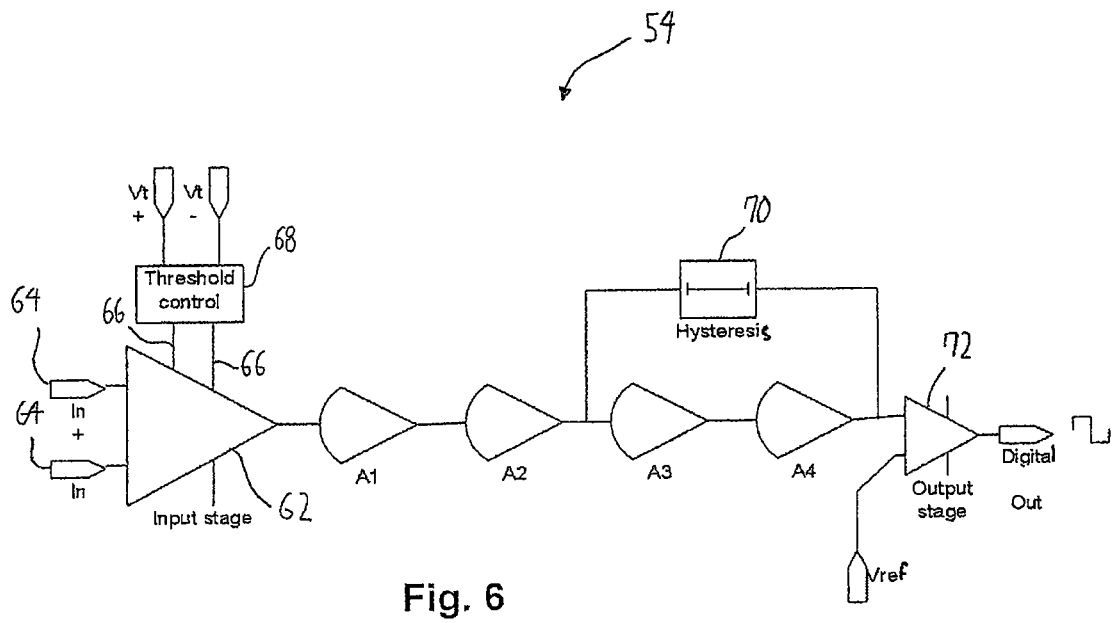
FIG. 6 shows an example of the fast pulse-modulation discriminator integrated in a monolithic CMOS technology.

FIG. 6 shows a conceptual diagram of the pulse modulation discriminator 54. The discriminator circuit 54 comprises an input stage 62 which is shown in greater detail in FIG. 7. The input stage 62 comprises inputs 64 for a current signal received from the preamplifier 52 (cf. FIG. 4A) and inputs 66 for receiving a threshold DC-current signal from a threshold control unit 68. With continued reference to FIG. 6, the discriminator circuit 54 comprises four differential amplifiers A1 to A4 connected in series by which the output of the input stage 62 is amplified. The discriminator circuit 54 further comprises a hysteresis or positive feed-back element 70 for increasing the stability of the output signal. Finally, the discriminator circuit 54 comprises an output stage 72 for shaping the output signal such as to acquire sharp rising and falling edges. The complete discriminator circuit 54 is integrated in monolithic CMOS technology.

Figure 7:
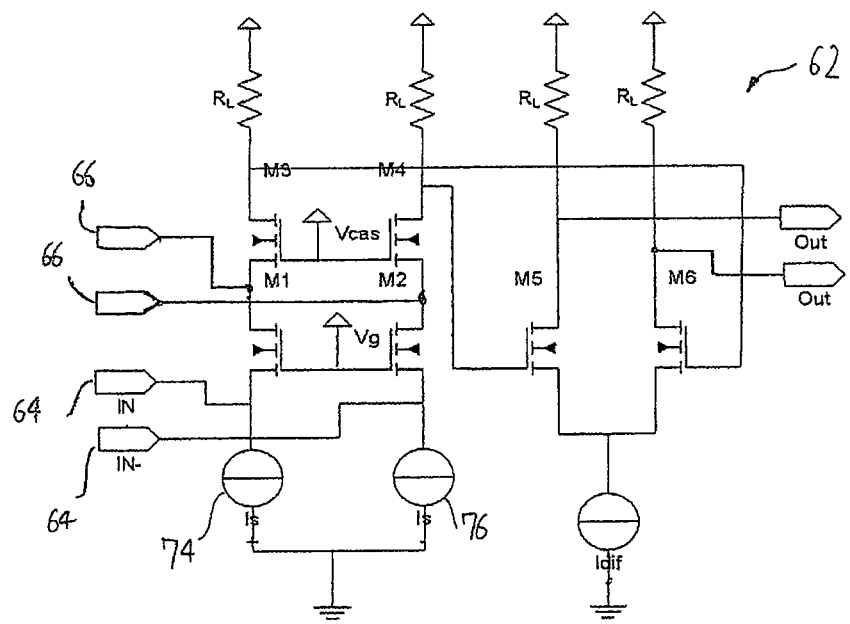
FIG. 7 shows an example of the input stage of the discriminator of FIG. 6.

In FIG. 7, the input stage 62 is shown in greater detail. As can be seen in FIG. 7, the input stage 62 comprises two symmetrically arranged current sources 74, 76 connected to transistors M1, M2, respectively. In addition, the input stage 62 comprises cascode transistors M3 and M4 connected with transistors M1, M2, respectively.

As is readily appreciated by the person skilled in the art, the input stage 62 of FIG. 6 provides a comparison of the signal current injected at inputs 64 and the threshold current injected at inputs 66.

It is noted that the discriminator circuit 54 as shown in FIGS. 6 and 7 as such is known from the article "NINO: An Ultrafast Low-Power Front-End Amplifier Discriminator for Time-of-Flight Detector in the ALICE Experiment" by F. Anghinolfi, P. Jarron, F. Krummenacher, E. Usenko and M. C. S. Williams, IEEE Transactions on Nuclear Science, vol. 51, No. 5, October 2004, pages 1974 to 1978, and from "NINO: An ultra-fast and low-power front-end amplifier/discriminator ASIC designed for the multigap resistive plate chamber", F. Anghinolfi, P. Jarron, A. N. Martemyanov, E. Usenko, H. Wenninger, M. C. S. Williams and A. Zichichi, Nucl. Instrum. Methods Phys. Res., A 533 (2004) 183-187. However, this discriminator has been employed in a very different context of time-of-flight detection of charged particles having energies in the GeV range in high energy physics experiments but not for the detection of photons and, in particular, not in the context of medical imaging. In particular, when the discriminator circuit 54 was used in high energy physics experiments, the energy of the detected particles was not encoded and could not even have been encoded, since in the prior art experimental setup the particles to be detected only transmitted a part of their energy to the detector and the information processed for the experiment comprised only binary if-data (hit or no-hit).

Figure 8:
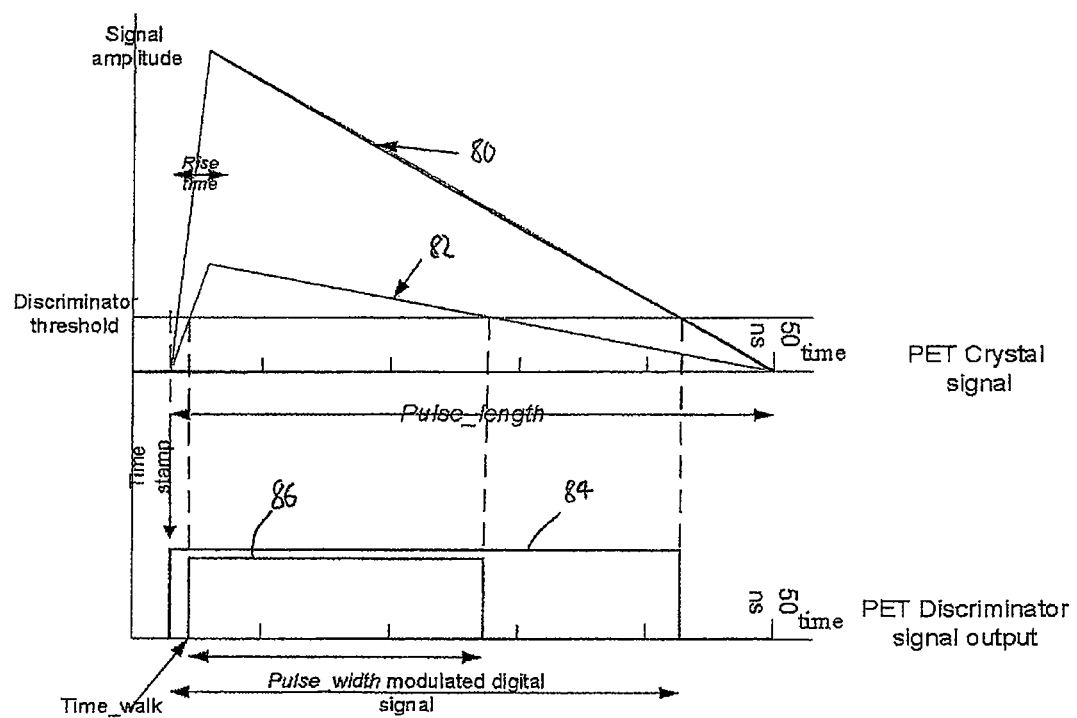
FIG. 8 shows a schematic timing diagram related to the pulse width modulation discriminator of FIG. 6 when operating in PET mode.

The upper diagram of FIG. 8 shows two simplified waveforms of detection signals 80, 82 inputted into the pulse modulation discriminator 54. The upper signal 80 corresponds to the detection of a photon of higher energy and the lower signal 82 corresponds to the detection of a photon of lower energy. The signal shape is a triangular shape approximating the typical response of a scintillator. That is, typically the scintillator has a characteristic rise time which is largely independent of the energy of the photon and a consecutive exponential decrease at a time constant on the order of 40 ns.

Also in the upper diagram, the discriminator threshold described with reference to FIGS. 6 and 7 above is shown. From the signals 80 and 82 and the discriminator threshold, the pulse modulation discriminator 54 generates respective pulses shown in the lower diagram as 84 and 86, respectively. The leading edge of the pulse signals 84, 86 corresponds to the time the signal 80, 82, respectively first exceeds the discriminator threshold, and the trailing edge of the pulse signal 84, 86 corresponds to the time the detection signal 80, 82, respectively drops below the discriminator threshold. As is clear from FIG. 8, the higher the amplitude of the signal, or in other words, the higher the energy of the detected photon, the wider the width of the pulse signal 84, 86 will be. Accordingly, the width of the pulse signals 84, 86 can be used for encoding the energy of the corresponding photon.

As can be seen from FIG. 8, the leading edges of the pulse signals 84, and 86 are not exactly coinciding with one another and in particular, are not coinciding with the true beginning of the signals 80 and 82. Instead, there is a delay corresponding to the time needed for the signals 80, 82 to reach the discriminator threshold. This delay is usually called "time-walk". Consequently, while the leading edge of the pulse signals 84, 86 do encode the time-stamp, said time-stamp should be corrected by the time-walk to provide high precision time measurements. As can be discerned from FIG. 8, the time-walk can be approximated by the following simplifying equation:

$$\text{time-walk} = \text{rise time} \frac{\text{discriminator threshold}}{\text{signal amplitude}}$$

Since the pulse width is related to the signal amplitude (in fact, for a considerable region it is almost proportional thereto), the time-walk can be determined from the pulse width. Accordingly, from the pulse signals 84 and 86 alone, a very precise time-stamp and a precise measurement of the energy can be obtained. Moreover, it is noted that such a pulse signal can be easily and rapidly processed, for example by a TDC as described below, allowing for a real time processing of the data and "on-line" generation of medical images.

With continued reference to FIG. 8, there will be a jitter related to the time uncertainty with which the signal 80, 82 crosses the threshold due to noise superimposed on the signal. Timing jitter is given by the general formula $\sigma_{jitter} = \sigma_n / |dV/dT|$ where $\sigma_n$ is the noise superimposed on the pulse and $dV/dT$ is the slope of the pulse at the point where it crosses the threshold. In the situation of FIG. 8, the jitter equation therefore reads as follows: $\sigma_{jitter} = \sigma_n$ $$\frac{\text{rise time}}{\text{signal amplitude}} = \frac{\text{rise time}}{\text{signal-to-noise ratio}}$$

Consequently, with a rise time of 1 ns and a threshold to amplitude ratio of 5 the time-walk is 200 ps and the jitter would be 20 ps with a signal-to-noise ratio of 50. Such a small jitter allows for very precise measurements, well-sufficient for time-of-flight measurements.

Figures 9, 10:
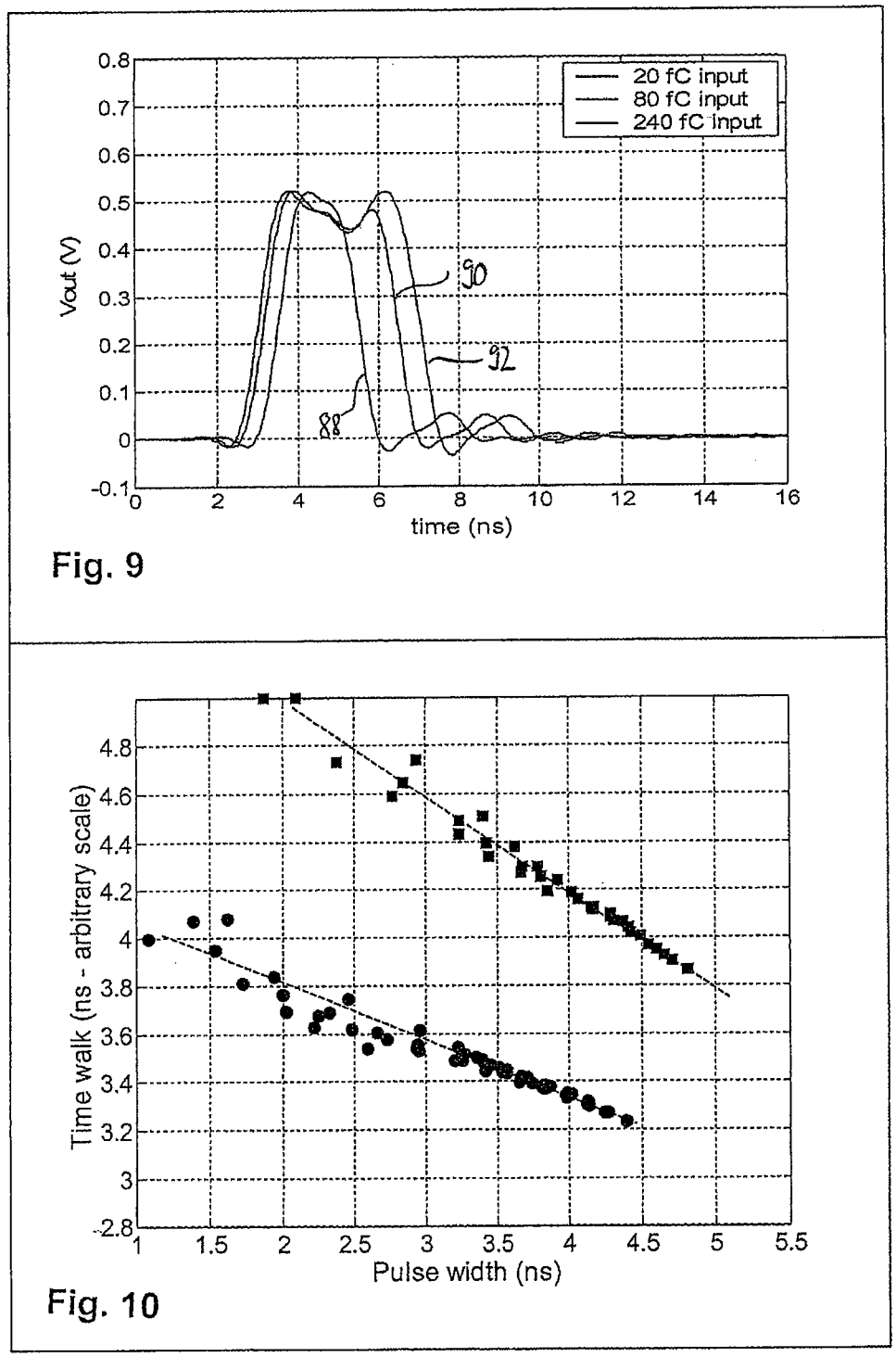
FIG. 9 shows an output waveform of experimental measurements obtained at the output of the pulse width modulation discriminator of FIG. 6.
FIG. 10 shows a relation between time-walk and pulse width as obtained with the discriminator circuit of FIG. 6.

FIG. 9 shows three output waveforms 88, 90 and 92 obtained in experiment with the pulse modulation discriminator 54 of FIG. 6. In this measurement, the input of the pulse modulation discriminator 54 has been stimulated with electronic pulses of 20 fC (curve 88), 80 fC (curve 90) and 240 fC (curve 92), respectively.

As can be seen from FIG. 9, the pulse width is directly related to the size or charge of the stimulation signal. Also, from FIG. 9 it can be seen that the pulse modulation discriminator even works with much faster signals than the ordinary scintillation signal as shown in FIG. 8. Clearly, the time resolution obtainable with the pulse modulation discriminator is well in the picosecond range allowing for precise time-of-flight measurements.

FIG. 10 shows measurements of the correction of the time-walk based on the discriminator pulse width indicating a timing precision easily in the range of the precision required for a TOF-PET-scanner system.

Figure 11:
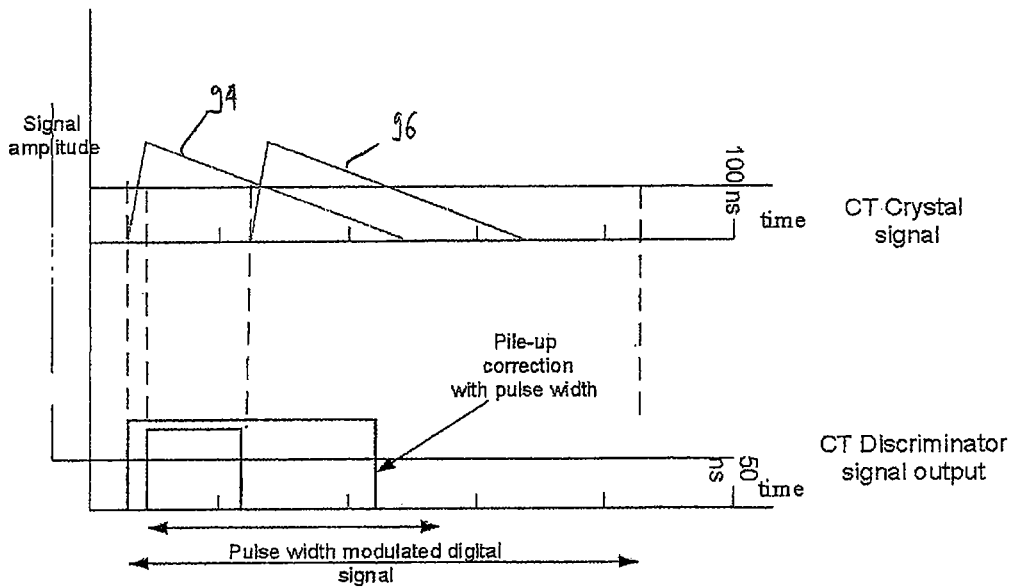
FIG. 11 shows a schematic timing diagram for the discriminator circuit of FIG. 6 operating in CT mode.

FIG. 11 is a timing diagram similar to the timing diagram of FIG. 8. In the upper diagram of FIG. 11, two detection signals 94, 96 are shown which are due to X-ray photons hitting the same detector segment. Comparing the X-ray signals 94 or 96 with the PET-signal 80, it can be seen that the PET-signal 80 is larger, since the PET-γ-photon has an energy of 511 keV which is considerably higher than the energy of typical X-ray photons used in CT having about 100 keV. However, the discriminator threshold of the pulse modulation discriminator 54 is adjusted such as to generate pulses for both, PET and CT events using the same discriminator circuit, the pulses only differing in their respective lengths.

Figure 14:
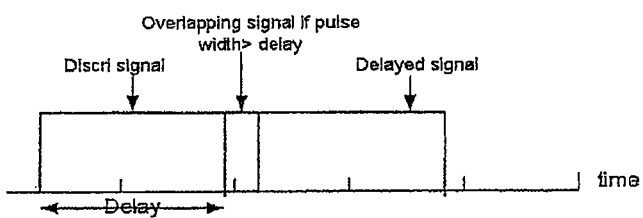
FIG. 14 is a conceptional drawing showing overlapping pulse signals.

In the situation shown in FIG. 11, the signals 94 and 96 overlap in time. This overlap or so called "pulse pile-up" frequently occurs at larger X-ray intensities. As can be seen from the lower diagram of FIG. 11, such an overlap of two X-ray signals will lead to a pulse signal which is wider than the pulse signal corresponding to a single X-ray photon. An example of the pulse signal due to two overlapping X-ray signals is also shown in FIG. 14. Overlapping pulse signals will occur if the width of the pulse signal corresponding to a single X-ray photon is larger than the delay time between two consecutive photons hitting the same detector segments.

Figure 12:
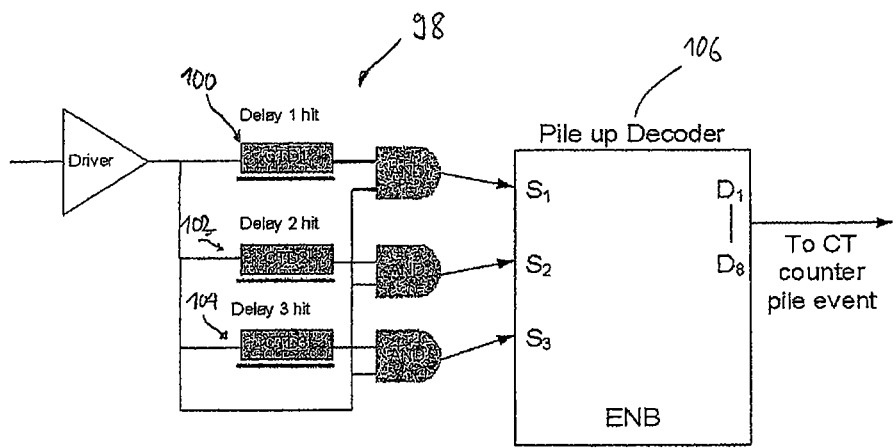
FIG. 12 is a circuit diagram for a filter for discriminating X-ray pulses overlapping in time.

In FIG. 12, a pulse pile-up filter 98 is shown. The pulse pile-up filter 98 comprises three basic gate-delay circuits 100, 102 and 104 which are connected in parallel. Each of the basic gate-delay circuits 100, 102, 104 comprises an AND-gate to which a fraction of the pulse signal and a delayed fraction of said pulse signal is fed, which delayed fraction is delayed by a predetermined time-delay. The basic gate-delay circuit 100 comprises a delay element providing for a time-delay corresponding to an expected width of the pulse signal for a single X-ray photon. Gate-delay circuits 102 and 104 each comprise a delay element providing for delays corresponding to an expected pulse width of the pulse signals for two or three overlapping X-ray detection signals, respectively. Accordingly, by using the pulse pile-up filter 98, two or three X-ray photons overlapping in time can be detected and distinguished. The outputs of the gate-delay circuits 100, 102, 104 are inputted to a pile-up decoder 106 for correcting a counter by one, two or three counts, depending on the output of the gate-delay circuits 100, 102 and 104.

Figure 13:
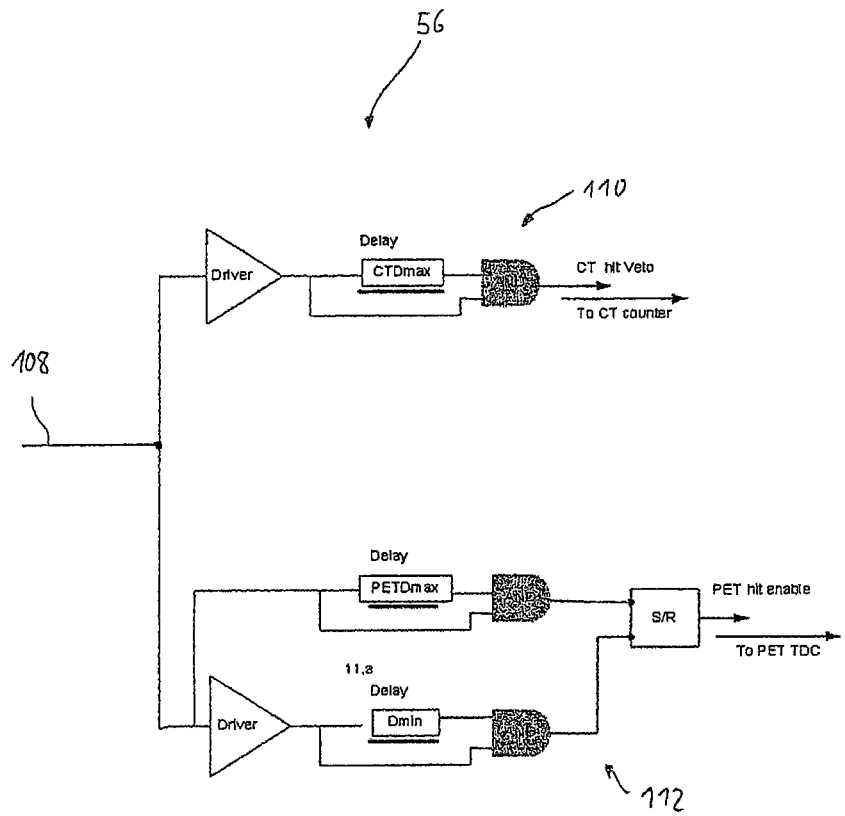
FIG. 13 is a circuit diagram showing filters for distinguishing CT-signals from PET-signals based on signal pulse width.

FIG. 13 shows an example of the PET-CT-filter 56 that has been shown generally in FIG. 4A. The PET-CT-filter circuit 56 has an input 108 for receiving a signal from the pulse modulation discriminator 54. The filter 56 comprises a CT branch 110 and a PET branch 112. In the CT branch, a gate-delay circuit is used to check whether the inputted pulse signal has a width longer than a predetermined delay time CTDmax. CTDmax may for example correspond to a pulse with corresponding to a photon having an energy of 120 keV. If the output of the AND-gate in the CT branch 110 is positive, this means that the detected pulse corresponds to a photon having an energy higher than said 120 keV and it can therefore not be an X-ray photon from the CT-X-ray source 48 of the apparatus 28 shown in FIG. 4. Consequently, this event is not counted by the corresponding CT counter.

In the PET-branch of the filter 56, it is checked whether the pulse width is longer than some predetermined delay PETDmax and longer than some minimal pulse width Dmin. With this filter, it can be checked whether the energy of the corresponding photon is within the range expected for PET-γ-photons. If the energy is within the expected range, the pulse signal will be channeled to the TDC 42 (see FIG. 4).

Figure 15:
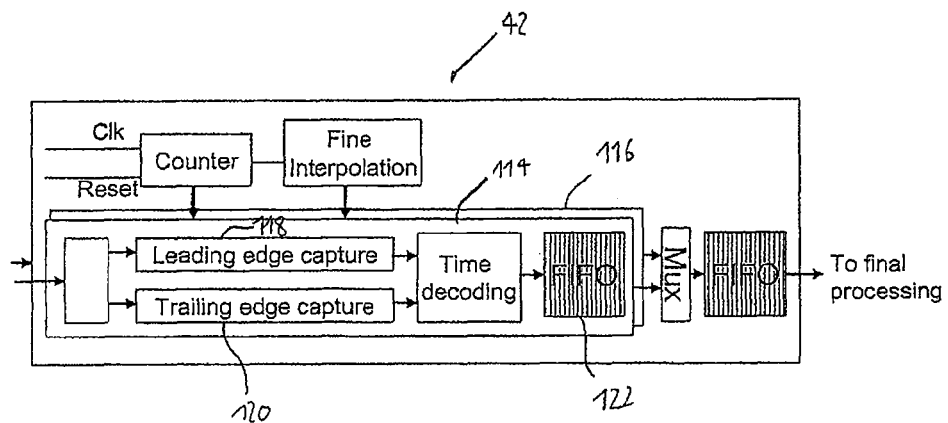
FIG. 15 shows a TDC-circuit architecture based on common clock reference.

In FIG. 15, a block diagram of a multichannel TDC circuit 42 is shown. For simplicity, in the multichannel TDC 42 of FIG. 15, only two channels, 114 and 116 are indicated. Each TDC channel 114, 116 receives pulse signals from the corresponding pulse modulation discriminator via a respective input. Each TDC channel 114 has means 118, 120 for leading and trailing edge capture, respectively. The leading edge of the pulse signal is time-walk corrected and decoded to yield a time-stamp. The difference between leading and trailing edge provides the energy or signal amplitude information. The time-stamp and energy information is stored in a local FIFO register 122. The basic TDC measurements of the leading and trailing edges of the pulse signal are performed in a fully clock synchronized fashion based on basic clock synchronized counters with sufficient dynamic range to cover the full period of data collection. A clock driven fine time interpolator circuit based on phase locked loops and/or delay locked loops driven from the same clock reference is used to obtain the required time resolution. This guarantees a continuously self-calibrating and very stable time measurement with very high time resolution (on the order of 10 ps) and very high operational stability.

As is schematically indicated in FIG. 15, multiple TDC channels can use the same time counters and fine interpolation units while using independent time capture circuits and a local FIFO 122. The time measurements from independent channels can be derandomized and merged into larger storage memories or FIFOs with an associated channel identifier and finally be transferred to the subsequent image processing.

Figure 16:
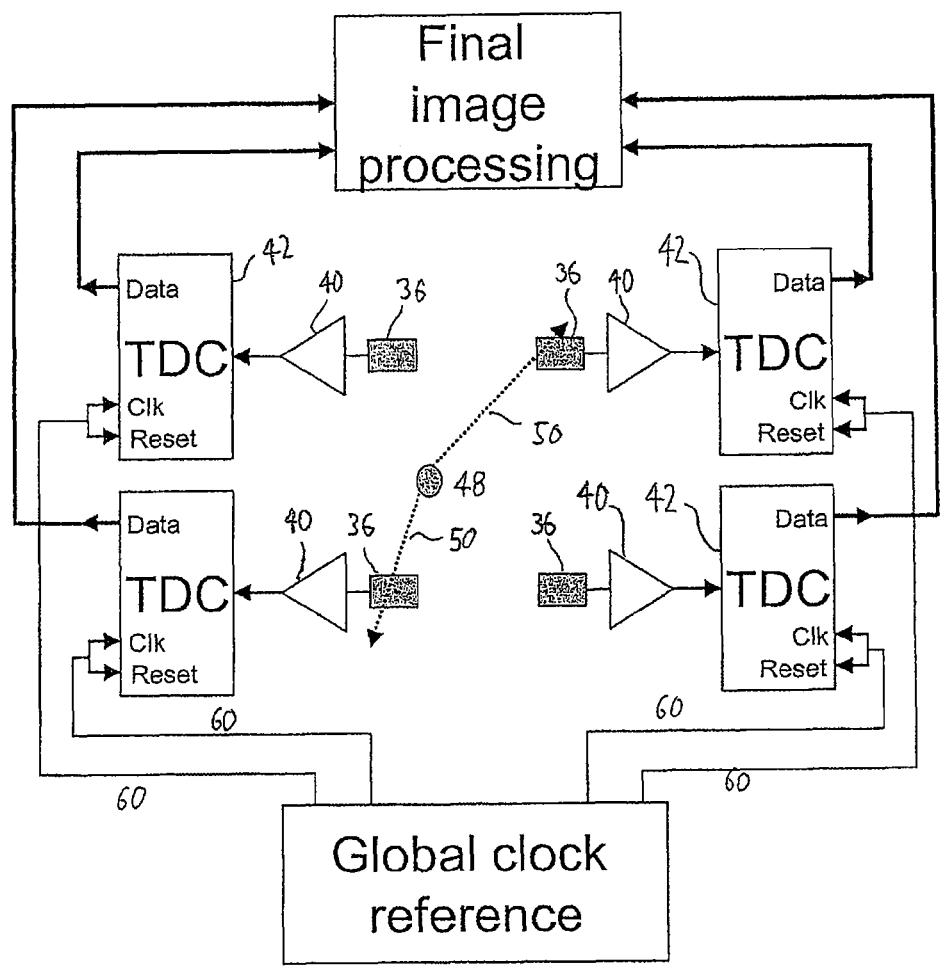
FIG. 16 is a block diagram illustrating a PET readout architecture employing TDCs with local time measurements based on global time reference.

FIG. 16 shows a block diagram of the PET readout architecture employing TDCs with local time measurements based on global time reference. In FIG. 16, again an annihilation site 48 is indicated from which γ-photons 50 are emitted. Also shown are four exemplary detection elements 34 and corresponding readout circuitry 40 and TDCs 42.

Each local TDC 42 is connected with a global reference clock 60. A global clock reference is distributed across the system with very small jitter together with a global clock synchronous reset signal defining a global zero time reference plus a time scale given by the repeated clock cycles.

Each TDC uses the received clock reference to measure the arrival time of the input signal edges. Consequently, only channel time offset parameters need to be determined from a simple global timing calibration to perform coincidence determinations and time-of-flight measurements across channels throughout the system.

As mentioned above, the present invention allows for a very precise time-stamp measurement of photons simultaneously with a precise measurement of the photon energy. The energy measurement has a number of important advantages. Generally, as has been mentioned above, by a precise energy measurement, the signal-to-noise ratio can be enhanced. First of all, due to the energy measurement, the envisaged photon events can be distinguished from background. Also, a precise energy measurement further allows to reconstruct Compton scattering of a γ-photon, that is, it allows to measure the energy of a photon and a corresponding electron after Compton scattering and to reconstruct the original photon therefrom.

Also, as has been explained with reference to FIG. 13, due to the measurement of the energy, it is possible to for example discriminate between X-ray photons and PET photons using the same front-end detection architecture, allowing for a very simple combined PET-CT apparatus. However, the energy discrimination could for example also be used to distinguish between photons of different wavelengths originating from different types of radiopharmaceuticals which are applied to a patient's body simultaneously. In such an embodiment, it is possible to investigate the location and concentration of different types of radiopharmaceuticals in only a single scan.

Figure 17:
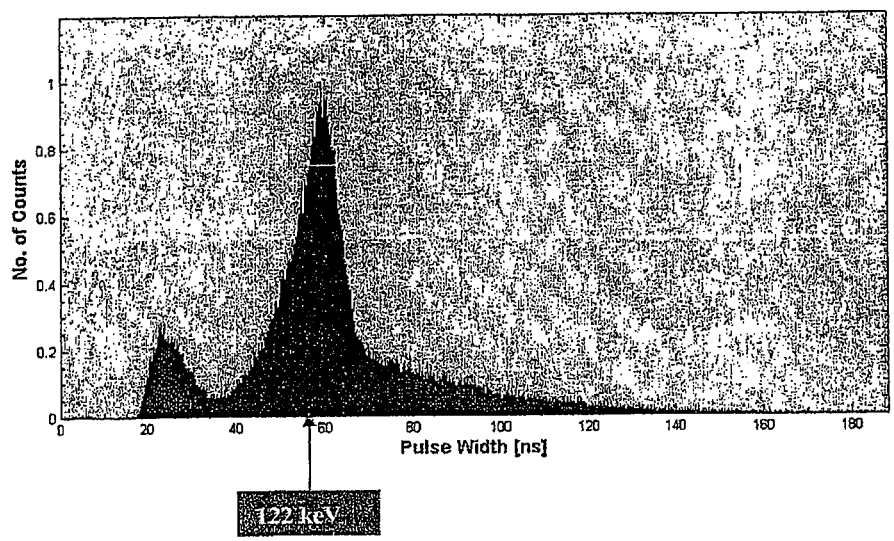
FIGS. 17 and 18 shows histogram plots of emission spectra obtained for $^{57}$Co, $^{22}$Na, respectively obtained with the readout architecture of the present invention.
Figure 18:
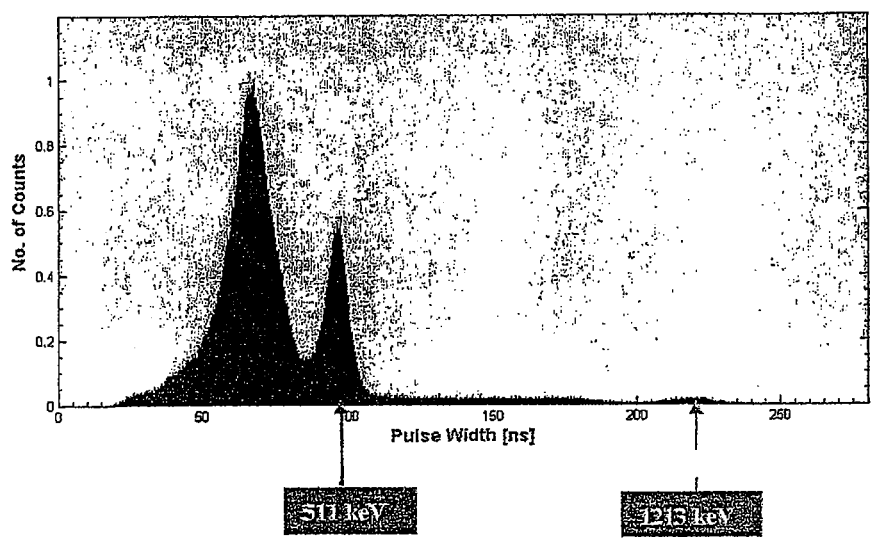

In FIGS. 17 and 18, the results of benchmark experiments related to the energy encoding are shown. In both diagrams, the horizontal axis denotes the pulse width as generated by the discriminator circuit 54 and the vertical axis represents the number of counts or detected events in a given period of time.

In particular, FIG. 17 is a histogram plot of the spectrum obtained using a $^{57}$Co radioactive source which has a photo peak located at an energy of 122 keV and is therefore a good benchmark for CT X-ray. The diagram of FIG. 18 represents a histogram plot of the spectrum obtained with a $^{22}$Na radioactive source with one photo peak located at an energy of 511 keV, which is a good reference for the PET γ-photon, and a second peak at 1213 keV. The plots represent experimental raw data without any correction and linearization. In order to get a correct energy scale, an offset of about 20 ns would be subtracted and a signal linearization should be applied. FIGS. 17 and 18 demonstrate that in fact a very precise energy measurement can be performed with the apparatus of the invention.

Although a preferred exemplary embodiment is shown and specified in detail in the drawings and the preceding specification, these should be viewed as purely exemplary and not as limiting the invention. It is noted in this regard that only the preferred exemplary embodiment has been shown and specified, and all variations and modifications should be protected that presently or in the future lay within the scope of protection of the invention as defined in the appending claims.

LIST OF REFERENCE NUMBERS

10 APD array
12 preamplifier
14 shaper
16 A/D converter
18 FIFO buffer
20 coincidence processor
22 current preamplifier
24 gated integrator
26 A/D converter
28 combined PET-CT-system
30 detector ring
34 detector element
36 scintillator array
38 photodetector array
40 front-end
42 TDC
44 coincidence processor
46 PET-CT-reconstruction processor
48 γ-photon
52 preamplifier
54 pulse modulation discriminator
56 filter
58 counter
60 global reference clock
62 input stage
64, 66 inputs
68 threshold control unit
70 feed-back element
72 output stage
74, 76 current sources
80 signal waveform
82 signal waveform
84 pulse signal
86 pulse signal
88-92 measured pulse signals
94, 96 overlapping X-ray signals
98 pulse pile-up filter
100-104 gate-delay circuits
106 pile-up decoder
108 input to filter 56
110 CT-branch
112 PET-branch
114, 116 TDC channels
118 leading edge capture means
120 trailing edge capture means
122 FIFO

The invention claimed is:

1. Apparatus for use in medical imaging, said apparatus comprising a readout circuit having an input for receiving a detection signal corresponding to a photon hitting a radiation detector, characterized in that the readout circuit is adapted to output, in response to receiving said detection signal, a pulse signal having a leading edge encoding a time-stamp of said photon and a width encoding an energy of said photon.

2. Apparatus according to claim 1, wherein said readout circuit is adapted for encoding the time-stamp and energy for one or more types of photons selected among a group consisting of: γ-photons as generated during electron-positron annihilation, X-ray photons of a wavelength suitable for CT, visible light photons, and γ-photons as emitted by radiopharmaceuticals suitable for γ-camera imaging or single photon emission computed tomography imaging.

3. The apparatus of claim 1 further comprising means for correcting the time-stamp based on the width of the pulse signal.

4. The apparatus of claim 3, wherein said correcting means are configured to estimate a time-walk of the pulse signal from the width of the pulse signal and to subtract the time-walk from the time-stamp.

5. The apparatus according to claim 1, wherein said readout circuit is a discriminator circuit configured to compare the detection signal to a threshold value, where the leading edge of the pulse signal corresponds to the time the detection signal first exceeds said threshold and the trailing edge of the pulse signal corresponds to the time the detection signal drops below said threshold value.

6. The apparatus of claim 1, wherein the readout circuit is a monolithic CMOS-device.

7. The apparatus according to claim 1, wherein the radiation detector comprises a scintillator element and a photodetecting element, said photodetecting element being arranged to receive light emitted from said scintillator element.

8. The apparatus according to claim 7, wherein said scintillator element comprises a $Lu_2SiO_5$ crystal or a LuYAP crystal.

9. The apparatus of claim 7, wherein said photodetecting element comprises at least one avalanche photodiode.

10. The apparatus according to claim 1, further comprising a filter for filtering the pulse signal according to its width.

11. The apparatus according to claim 10, wherein the filter comprises at least one gate-delay circuit comprising an AND-gate to which a fraction of said pulse signal and a delayed fraction of said pulse signal is fed, said delayed fraction being delayed by a predetermined time-delay.

12. The apparatus according to claim 10, wherein the filter comprises a PET-filter configured to pass pulse signals having a width corresponding to the energy of γ-photons emitted during electron-positron annihilation.

13. The apparatus of claim 12, wherein the PET-filter blocks pulse signals having a width corresponding to an energy of less than 350 keV.

14. The apparatus according to claim 10, wherein the filter comprises a CT-filter configured to allow pulse signals having a width corresponding to the energy of X-ray photons suitable for CT to be counted by a counter.

15. The apparatus according to claim 14, wherein the CT-filter blocks pulse signals having a width corresponding to an energy of more than 250 keV.

16. The apparatus according to claim 1, further comprising a filter for distinguishing pulse signals corresponding to two or more detection signals corresponding to individual X-ray photons overlapping in time.

17. The apparatus of claim 16, wherein the filter comprises a number of n gate-delay circuits connected in parallel, each gate-delay circuit comprising an AND-gate to which a fraction of said pulse signal and a delayed fraction of said pulse signal is fed, said delayed fraction being delayed by a predetermined time-delay, wherein n is an integer greater or equal to 2, wherein the predetermined time-delays of the gate-delay circuits respectively correspond to an expected width of the pulse signal for one, two, . . . , n overlapping detection signals corresponding to X-ray photons overlapping in time.

18. The apparatus according to claim 1, further comprising a counter for counting the number of X-ray photons detected during a predetermined time period.

19. The apparatus of claim 1, further comprising a time-to-digital converter (TDC) connected to receive the pulse signal and configured to measure the arrival time of both the leading and trailing edge of the pulse signal.

20. The apparatus according to claim 19, wherein the TDC is configured to store the leading edge time measurement and the pulse width in a local channel FIFO register.

21. Detection assembly for a medical imaging apparatus, comprising a multitude of apparatuses according to claim 1.

22. The detection assembly according to claim 21, wherein some or all of the multitude of detector elements are connected to a common reference clock.

23. A combined PET-CT-apparatus comprising an X-ray generator suitable for CT and a detection assembly according to claim 21.

24. Detection assembly for a medical imaging apparatus, and in particular for a PET or a PET-CT-apparatus, said detection assembly comprising a multitude of detector elements, each detector element comprising an array of radiation detectors providing a number of channels for outputting detection signals and a corresponding number of apparatuses according to claim 1 providing electronic channels for reading out the detection signals.

25. The detection assembly of claim 24, further comprising a control unit configured or programmed for detecting coincidence of detection signals.

26. The detection assembly according to claim 25, wherein said control unit is further configured or programmed to calculate the location of an electron-positron annihilation using a difference in time-stamp of the coinciding events.

27. A method of reading out detection signals from a radiation detector of a medical imaging apparatus, said method comprising the steps of:
receiving an analog detection signal from a radiation detector upon a photon hitting said radiation detector, generating from said detection signal a pulse signal having a leading edge encoding the time-stamp of said photon hitting said radiation detector and a width encoding the energy of said photon.

28. The method according to claim 27, wherein said photon can be of one or more types selected among a group consisting of: γ-photons as generated during electron-positron annihilation, X-ray photons of a wavelength suitable for CT, visible light photons, and γ-photons as emitted by radiopharmaceuticals suitable for γ-camera imaging or single photon emission computed tomography imaging.

29. The method of claim 27, further comprising a step of correcting the time-stamp based on the width of the pulse signal.

30. The method of claim 29, wherein the correction step includes estimating a time-walk based on the width of the pulse signal and subtracting said time-walk from said time-stamp.

31. The method according to claim 27, in which the step of generating said pulse signal comprises a comparison of the detection signal with a threshold value, wherein the rising edge of the pulse signal corresponds to the time said detection signal first exceeds said threshold,
and the trailing edge of said pulse signal corresponds to the time the detection signal drops below said threshold.

32. The method according to claim 27, further comprising a step of filtering each pulse signal according to its width.

33. The method according to claim 32, wherein the filtering comprises directing pulse signals having a width corresponding to the energy of a γ-photon emitted during electron-positron annihilation to a TDC.

34. The method according to claim 32, wherein the filtering comprises allowing pulse signals having a width corresponding to the energy of an X-ray photon used in CT to be counted.

35. The method according to claim 32, wherein the filtering comprises a determination of whether the width of the pulse signal corresponds to an expected width occurring when the detection signal corresponding to two or more X-ray photons overlap in time.

36. The method according to claim 27, comprising a step of receiving the pulse signal at a TDC and measuring the arrival time of both the leading and the trailing edge of the pulse signal.

37. The method according to claim 36, said method further comprising a step of storing the leading edge time measurement and the pulse width in a local channel FIFO register.

38. The method according to claim 27, further comprising a step of coincidence detection of two detection signals corresponding to the two γ-photons originating from electron-positron annihilation.

39. The method according to claim 38, further comprising a step of calculating the location of the electron-position annihilation using a difference in time-stamp of the coinciding events.

* * * * *

UNITED STATES PATENT AND TRADEMARK OFFICE
CERTIFICATE OF CORRECTION

PATENT NO.        : 8,598,536 B2                                                              Page 1 of 1
APPLICATION NO. : 12/444295
DATED             : December 3, 2013
INVENTOR(S)       : Jarron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1277 days.

Signed and Sealed this
Twenty-second Day of September, 2015

Michelle K. Lee
*Director of the United States Patent and Trademark Office*